(12) United States Patent
Haberstich

(10) Patent No.: US 8,652,165 B2
(45) Date of Patent: Feb. 18, 2014

(54) TOGGLING ERGONOMIC SURGICAL INSTRUMENT

(75) Inventor: Wells D. Haberstich, Loveland, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 2 days.

(21) Appl. No.: 13/455,373

(22) Filed: Apr. 25, 2012

(65) Prior Publication Data

US 2013/0289541 A1    Oct. 31, 2013

(51) Int. Cl.
*A61B 17/00* (2006.01)

(52) U.S. Cl.
USPC ............... 606/205; 600/197; 600/218

(58) Field of Classification Search
USPC ............ 606/51, 52, 167, 170, 171, 174, 606/205–208; 30/134, 191, 211, 235, 250, 30/252, 272.1, 312, 363, 526; 600/131, 600/197, 214, 226, 218; 74/473.3, 483 PB, 74/543; 83/729
See application file for complete search history.

(56) References Cited

U.S. PATENT DOCUMENTS

| 6,214,028 | B1* | 4/2001 | Yoon et al. ................. 606/205 |
| 2002/0072766 | A1 | 6/2002 | Hunt et al. |
| 2004/0158233 | A1 | 8/2004 | Dicesare et al. |
| 2009/0209991 | A1* | 8/2009 | Hinchliffe et al. ........... 606/170 |
| 2009/0326564 | A1* | 12/2009 | White et al. ................. 606/148 |

FOREIGN PATENT DOCUMENTS

| EP | 0827715 A2 | 3/1998 |
| WO | 95/10230 A1 | 4/1995 |
| WO | 00/09021 A1 | 2/2000 |

OTHER PUBLICATIONS

International Search Report dated Jun. 28, 2013, International Application No. PCT/US2013/036754.

* cited by examiner

*Primary Examiner* — Ryan Severson
*Assistant Examiner* — Katherine M Shi

(57) ABSTRACT

A ergonomic surgical instrument is provided having a first and second trigger. The instrument comprises a shroud and at least one toggle switch located on the shroud's lateral surface for selectively engaging the first or second trigger to actuate an end-effector. The toggle fixes the position of one trigger with respect to the shroud while permitting the other trigger to actuate the end-effector.

12 Claims, 14 Drawing Sheets

TOGGLING ERGONOMIC SURGICAL INSTRUMENT

BACKGROUND

The present invention relates in general to surgical devices and procedures. Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed.

Endoscopic surgical instruments generally comprise an end-effector attached to an elongated shaft, which may be rigid or flexible, and the shaft is, in turn, attached to a handle assembly. The endoscopic surgical instrument is passed through the trocar where the end-effector and a portion of the shaft enter the insufflated cavity while a portion of the shaft and the handle assembly remains outside the insufflated cavity. During surgical procedures, the trocar may serve as a fulcrum about which the shaft is moved.

The handle assembly in some endoscopic instruments is oriented transverse to the shaft of the instrument, which is sometimes referred to as a pistol-grip. Some endoscopic instruments have the handle assembly arranged in the same plane as the shaft and are sometimes referred to as scissor grip. Pistol grip and scissor grip surgical instruments often comprise two triggers arranged for actuation in a co-planar manner. In this arrangement, one handle is often stationary while the other handle moves which in turn moves the end-effector. While endoscopic surgical instruments are known, no one has previously made or used the surgical devices and methods in accordance with the present invention.

SUMMARY

In one embodiment a surgical instrument, comprises a distal end effector and a proximal handle. The handle may comprise first and second triggers each being operably connectable to the end effector. A toggle has a first position and a second position. In the first position the first trigger is locked relative the handle and the second trigger is moveable relative the handle to actuate the end effector. In the second position the second trigger is locked relative the handle and the first trigger is moveable relative the handle to actuate the end effector. The surgical instrument may further comprise an elongate shaft extending between the end effector and the handle. The handle and triggers may be arranged in a pistol-grip configuration. The handle and triggers may also be arranged in a scissors-grip configuration.

The handle may further comprise a shroud. The toggle may comprise a first toggle switch and a second toggle switch. The first and second toggle switches may be disposed substantially opposite each other on the shroud defining an axis. A pin may be slideably disposed along the axis in mechanical communication with the first and second toggle switches and selectively engageable with the first trigger or the second trigger.

In another embodiment, an ergonomic surgical instrument comprises a shroud, a first trigger pivotally connected to the shroud, and a second trigger pivotally connected to the shroud. A link may be located within the shroud along with a shaft in communication with the link capable of transferring motion to an end-effector. A first toggle switch and a second toggle switch are disposed substantially opposite each other on the shroud's lateral surface and define an axis. A pin may be slideably disposed within the link along the axis in mechanical communication with the first and second toggle switches and selectively engageable with the first trigger or the second trigger.

The instrument may further comprising a first toggle position wherein the first toggle switch engages the second trigger fixing the second trigger relative to the shroud and moving the pin into engagement with the first trigger permitting the first trigger to move the link. The instrument may further comprise a second toggle position wherein the second toggle switch engages the first trigger fixing the first trigger relative to the shroud and moving the pin into engagement with the second trigger permitting the second trigger to move the link.

The instrument may comprise an end-effector disposed at the shaft distal end. Movement of the first trigger may create longitudinal force along the shaft moving the end-effector. Movement of the second trigger may create longitudinal force along the shaft moving the end-effector. The first toggle switch may comprise detents to selectively fix the first toggle switch in position relative to the shroud. The shaft may comprise a pushrod. The shaft may be adapted for use in endoscopic surgery.

In yet another embodiment, an ergonomic surgical instrument comprises a shroud, a first trigger pivotally connected to the shroud, and a second trigger pivotally connected to the shroud. A link may be located within the shroud. A shaft is capable of transferring motion to an end-effector in communication with the link. A means is provided for alternately engaging the shaft by either the first or second trigger. The shaft may comprise a pushrod. The end-effector may be disposed in a scissor arrangement. The end-effector may be comprised of a stationary jaw member and a movable jaw member in mechanical communication with the shaft.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Figure 1:
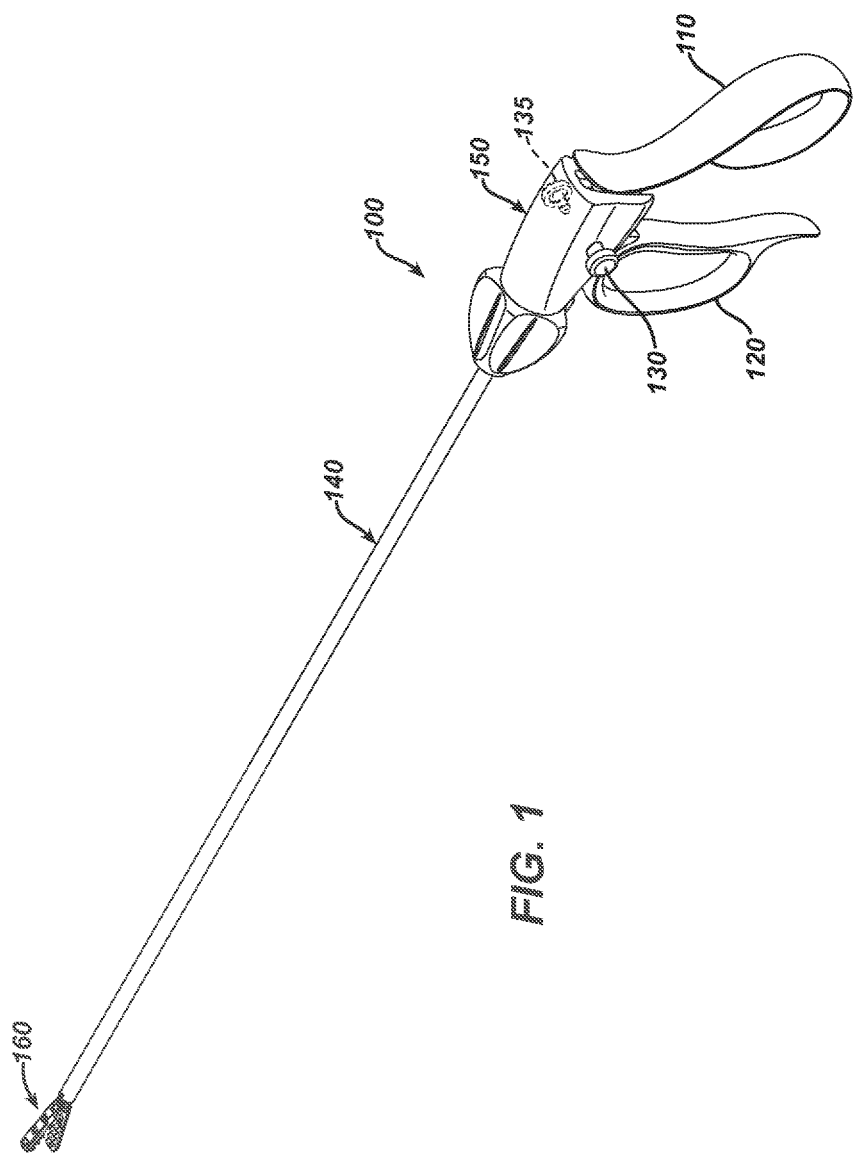
FIG. 1 depicts an isometric view of a surgical instrument having a dual action handle assembly.

The devices and methods disclosed herein relate to surgical instruments and more particularly, ergonomic surgical instruments having a handle. During endoscopic surgery, a trocar is typically inserted through an abdominal wall allowing access to the abdominal cavity. Long shafted instruments may be passed through the trocar to perform a surgical procedure. Those long shafted instruments generally have a handle in the form of a pistol grip or scissor grip. These instruments may be manually powered such as graspers and dissectors and may employ electrical or mechanical energy at the end effector, as is known and understood in the art. Expressions of an ergonomic surgical instrument grip will be described in detail with reference to drawings wherein like reference numerals designate identical or corresponding elements in each of the several views.

For purpose of explanation and illustration and not limitation, an isometric view of one expression of an ergonomic surgical instrument handle assembly is shown in FIG. 1 and is designated by reference number 100. Other expressions of ergonomic surgical instruments are presented in FIGS. 2-14, as will be described fully herein.

Referring to FIG. 1, ergonomic instrument is comprised of a thumb trigger 110 pivotally attached to handle shroud 150. Instrument 100 is further provided with finger trigger 120 pivotally attached to shroud 150. Instrument 100, as shown in FIG. 1, comprises an elongated rigid shaft 140. Alternatively, instrument 100 may be provided with a flexible shaft for use in flexible endoscopy (not shown). Shaft 140 may be adapted for use in open surgical procedures. In one expression, the instrument 100 includes a toggle mechanism comprising a thumb trigger lock toggle switch 130 and a finger trigger lock switch 135, both being movably attached to shroud 150 lateral surface.

Instrument 100, as is shown in FIG. 1, is provided with a grasper end effector 160. It is contemplated that instrument 100 may be provided with any jaw-type end effector including scissors, graspers, dissectors and may further employ ultrasonic energy and RF energy. It is contemplated that end-effector 160 may have one stationary jaw and one movable jaw.

Figure 2:
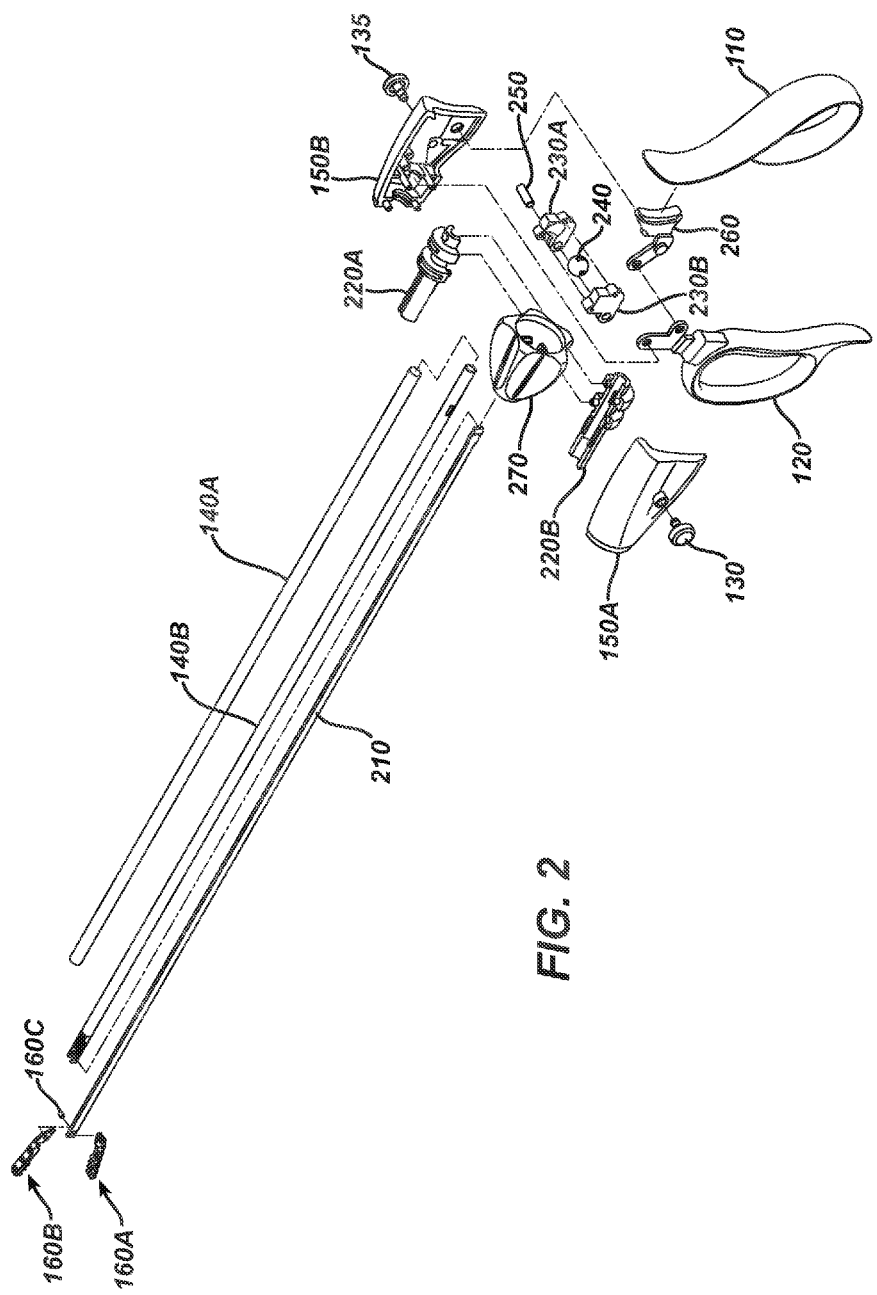
FIG. 2 depicts an exploded isometric view of a surgical instrument having a dual action handle assembly.

Referring now to FIG. 2, an exemplary embodiment of instrument 100 is shown in exploded view. Shaft 140 comprises outer tube 140A, inner tube 140B located medial to tube 140A. Pushrod 210 is located medial to tube 140B and is, in one expression, of rigid construction. Pushrod 210 may be comprised of metal, plastic or any other material suitable for surgical applications. Outer tube 140A may be comprised of metal, plastic or any other atraumatic material.

Pushrod 210 is pivotally connected to jaw members 160A and 160B via pin 160C as is known and understood in the art to facilitate scissoring of end-effector 160. Shaft assembly 140 is rotatably connected to shroud 150 via shaft coupler 220, shown as shaft coupler halves 220A and 220B. Shaft coupler is rotatably attached to shrouds 150A and 150B and is fixedly attached to rotation knob 270, which permits rotation of shaft 140. Proximal end of pushrod 210 is fixedly attached to slotted ball 240 via pin 250.

Slotted ball 240 is in rotatable contact with link 230. As shown in FIG. 2, link 230 comprises two halves 230A and 230B which partially enclose ball 240 and permit the transfer of longitudinal force from handles 110 or 120 to pushrod 210 which, in turn, actuates end-effector 160. Pin 250, in one expression, slideably engages link 230 and ball 240. Toggle switches 130 and 135 engage pin 250 permitting handle movement selection.

Figure 3:
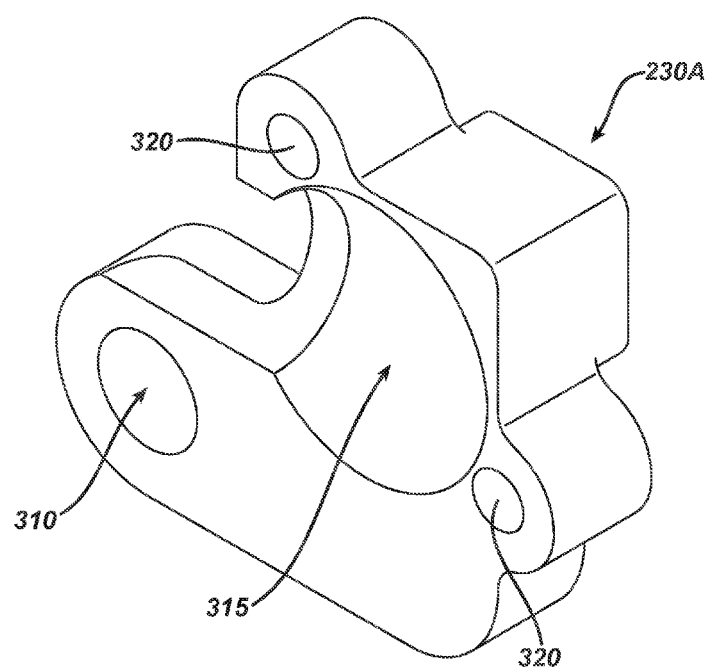
FIG. 3 is an isometric view of a one half of a handle-shaft link assembly.

Referring to FIG. 3, an isometric view of a one half of a handle-shaft link assembly 230A is shown. Link 230A, as shown, is of unitary construction but it is contemplated that link 230A may be comprised of multiple components. Link 230A mates with link 230B via annuli 320 to form an longitudinal interference fit with ball 240. Link 230A and link 230B have medial impressions 315 (link 230B not shown) designed to partially enclose ball 240. Impression 315 is sized to permit ball 240 to rotate when enclosed between links 230A and 230B but to prevent ball 240 from moving longitudinally relative to links 230A and 230B. Link 230A and 230B (not shown) have an annular opening 310 at a distal end to permit the lateral movement of pin 250 therethrough.

Figure 4:
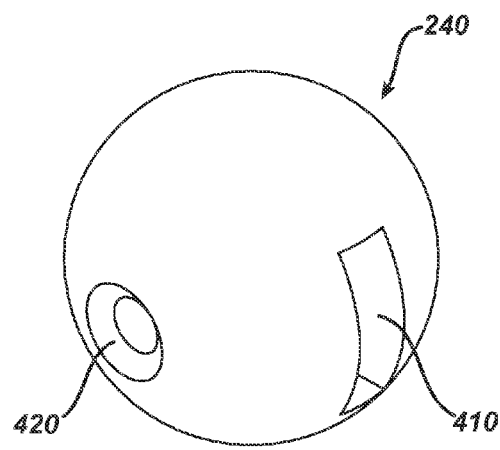
FIG. 4 is an isometric view of a pushrod ball.

Ball 240, in one expression, may be provided with slot 410, shown in FIG. 4. It is contemplated that slot 410 is sized to permit distal end of pushrod 210 to pass at least partially into ball 240. Ball 240 is provided with annular opening 420 that permits passage of a pin (not shown) at least partially through ball 240 and into pushrod 210 proximal end to create an interference fit between ball 240 and pushrod 210. It is contemplated that ball 240 may be molded onto the proximal end of pushrod 210 or may be formed as part of pushrod 210, as is known in the art. Ball 240 is sized to fit within link 230 and to rotate within link 230 permitting rotation of end-effector 160.

Figure 5:
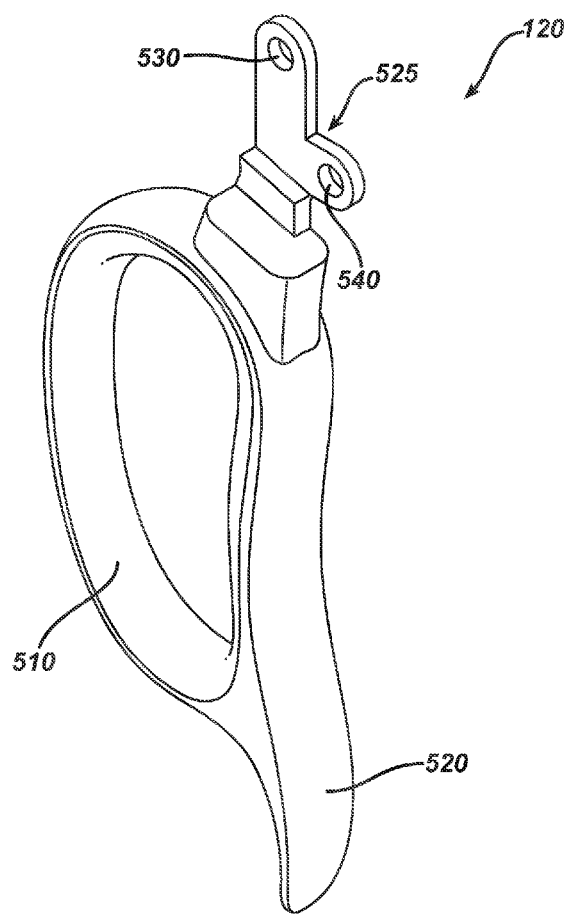
FIG. 5 is an isometric view of a finger trigger.

Referring now to FIG. 5, an isometric view of finger trigger 120 is shown. As depicted, finger trigger 120 comprises a closed finger ring 510 adapted to accommodate multiple fingers of a surgeon. In another expression, finger trigger 120 may be a shepherd's hook as is known in the art. Finger trigger 120 may be provided with finger hook 520 to accommodate a surgeon's finger outside of finger ring 510. Trigger 120, in one expression, comprises a linkage 525 having a shroud engagement annulus 530 and an annulus 540 adapted to engage toggle switch 130 and pin 250. In one expression, annuli 530 and 540 are oriented in an L-shaped fashion, but it is contemplated that multiple geometries may be employed to permit selective actuation of finger trigger 120.

Figure 6:
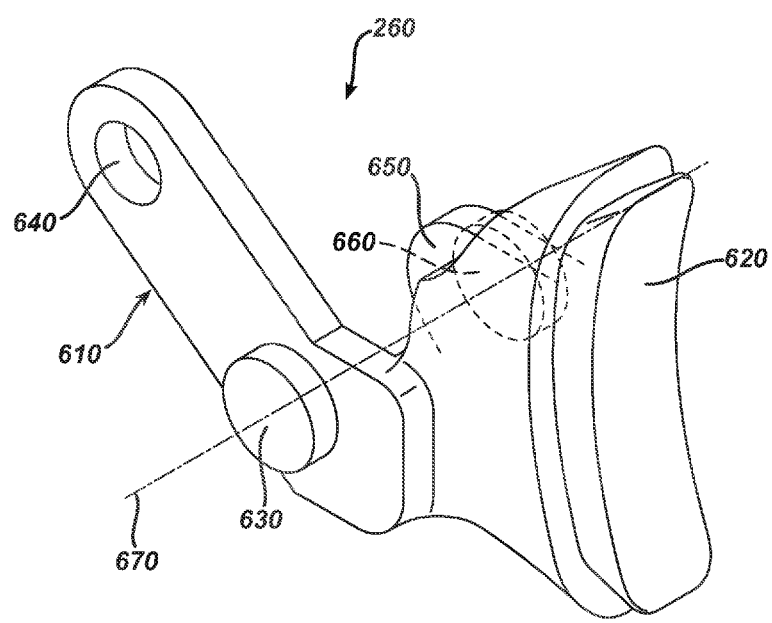
FIG. 6 is an isometric view of a thumb trigger linkage.

Thumb trigger 110 is provided with linkage 260, as is shown in FIG. 6. In one expression, linkage 260 and thumb trigger 110 are of non-unitary construction. It is contemplated that thumb trigger 110 and linkage 260 may be molded as a single piece. Linkage 260 is provided with mating surface 620 which may be adapted to produce a friction-fit with thumb trigger 110. Linkage 260 is further provided with a distal projecting arm 610 adapted to rotatably engage shroud 150A via cylindrical projection 630 and pin 250 via lever arm annulus 640. Trigger 110, in one expression, comprises a second lever arm 650 adapted to pivotally engage shroud 150B. In the FIG. 6 expression, second lever arm 650 is provided with annulus 660 adapted to rotatably engage a pin or boss projecting from shroud 150B medial surface (not shown).

Figure 7:
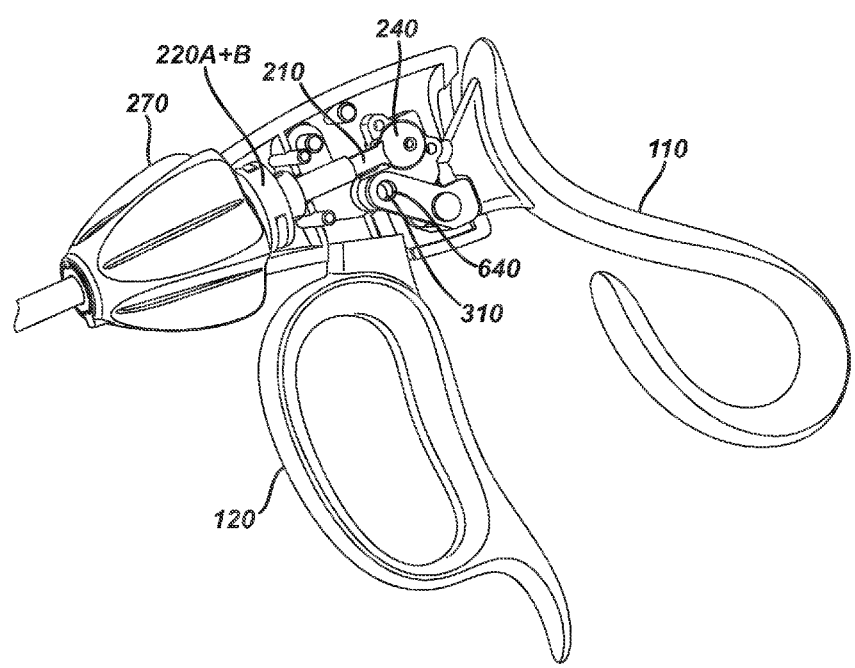
FIG. 7 is a partial cross sectional view of a handle assembly depicting thumb trigger linkage with half of the handle-shaft link assembly removed showing the pushrod ball.
Figure 8:
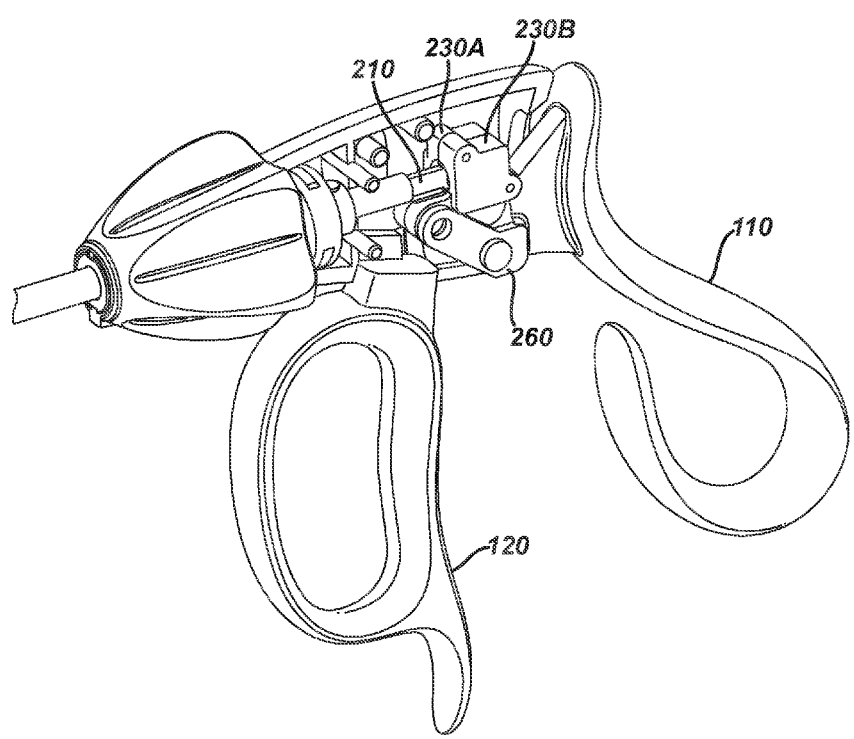
FIG. 8 is a partial cross sectional view of a handle assembly with a complete handle-shaft link assembly and thumb trigger linkage.

Referring now to FIG. 7, a partial cross sectional view of a handle assembly depicting thumb trigger linkage 610 with half of the handle-shaft link 230B assembly removed showing the pushrod ball 240 located therein. Pushrod 210 is depicted having moved in a distal manner. In this view, annuli 640 and 310 are aligned to permit passage of pin 250 therethrough. FIG. 8 depicts the FIG. 7 cross-sectional view with link 230B engaged with link 230A partially enclosing ball 240. In this view, impressions 315 encircle ball in a manner that permits link 230 to translate vertically with respect to pushrod 110 longitudinal axis.

Figure 9:
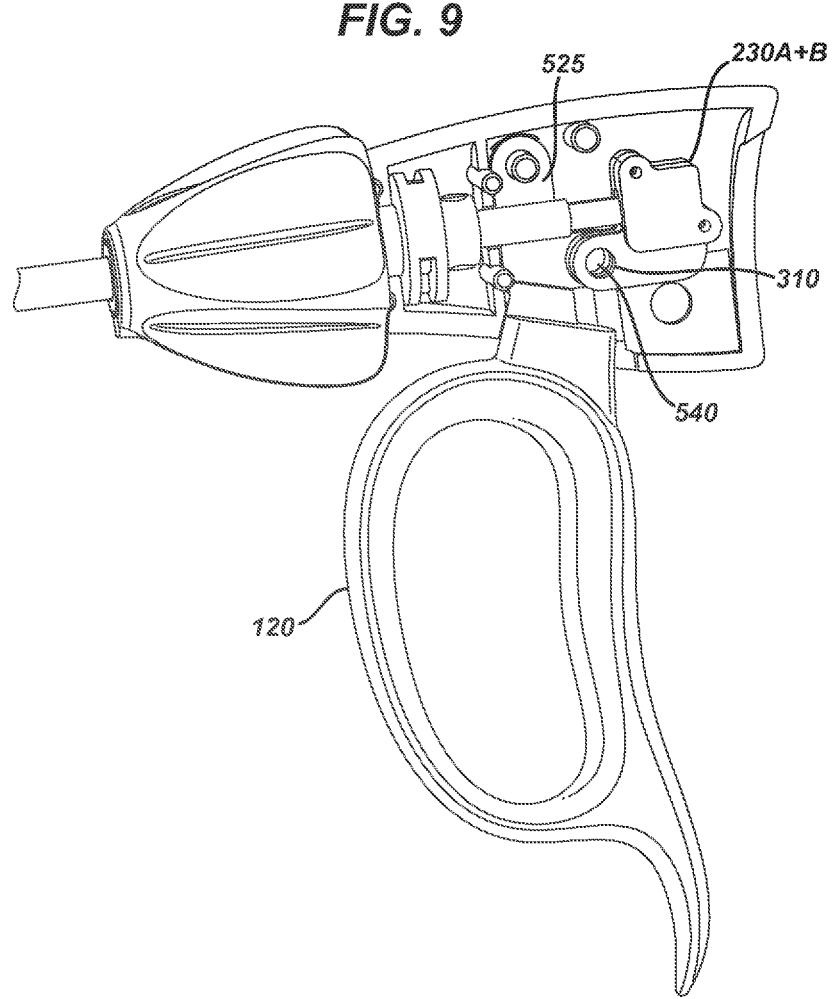
FIG. 9 is a partial cross sectional view of a handle assembly depicting finger trigger linkage engaging the handle shaft link assembly.

Referring now to FIG. 9, a partial cross sectional view of a handle assembly is depicted showing finger trigger linkage 525 engaging the handle shaft link 230 assembly. In this view, pin 250 is removed showing alignment of annulus 540 with link 230 annuli 310.

Figure 10:
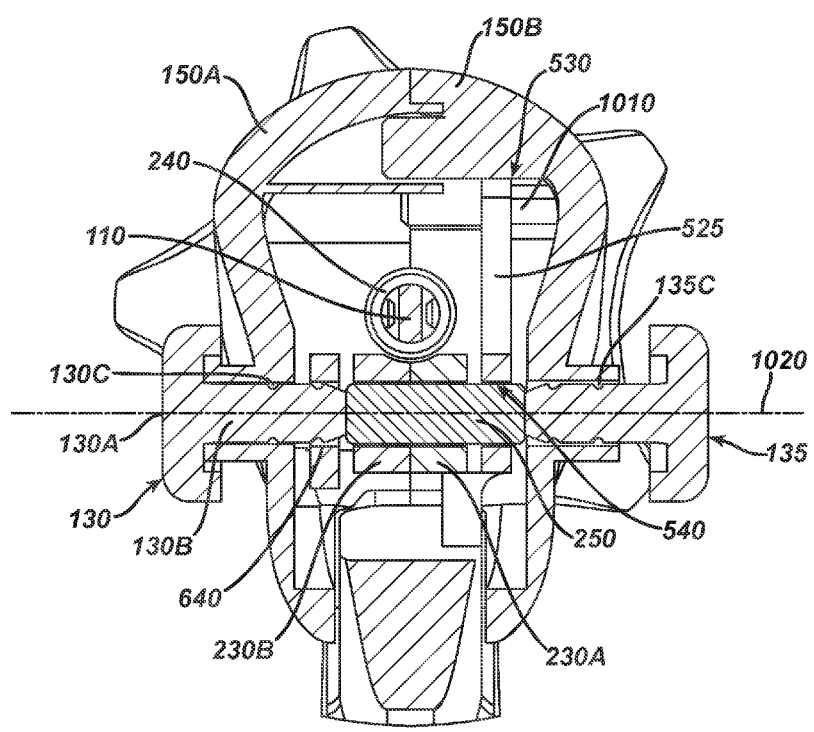
FIG. 10 is a cross sectional view of a toggle-linkage assembly with the thumb trigger locked and the finger trigger in a first position.

FIG. 10 depicts a cross sectional view of a toggle-linkage assembly with the thumb trigger 110 locked and the finger trigger 120 in a first position. Toggles 130 and 135 and pin 250 define an axis 1020. As shown, toggle flange 130A is moved to a position in contact with shroud 150A. Toggle stud 130B, in one expression, is provided with detents 130C which may permit predictable movement of toggle 130 medially and laterally. Stud 130B engages pin 250 moving pin 250 laterally along axis 1020 to engage finger trigger annulus 540 and link 230. In this configuration, finger trigger 120 is permitted to move link 230 longitudinally. When toggle 130 is depressed medially, pin 250 moves medially along axis 1020 moving toggle 135 laterally, disengaging toggle 135 from annulus 540 permitting finger trigger 120 to move link 230 longitudinally. Toggle stud 130B engages annulus 640 locking thumb trigger in a fixed position relative to shroud 150A.

Figure 11:
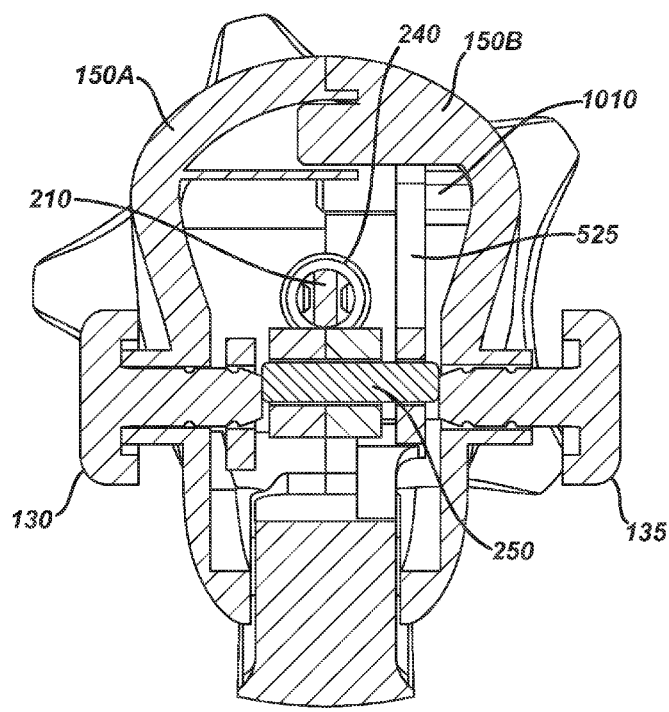
FIG. 11 depicts the FIG. 10 cross sectional view with the finger trigger moved to a second position.

When finger trigger 120 is moved to a second position, annulus 530 rotates about boss 1010 and linkage 525 pivots about boss 1010 generating longitudinal and vertical movement of link 230 as is shown in FIG. 11. Link 230 vertical and longitudinal translation about ball 240 creates a longitudinal force along pushrod 210. In this configuration, longitudinal force is translated along pushrod 210 to end-effector 160.

Figure 12:
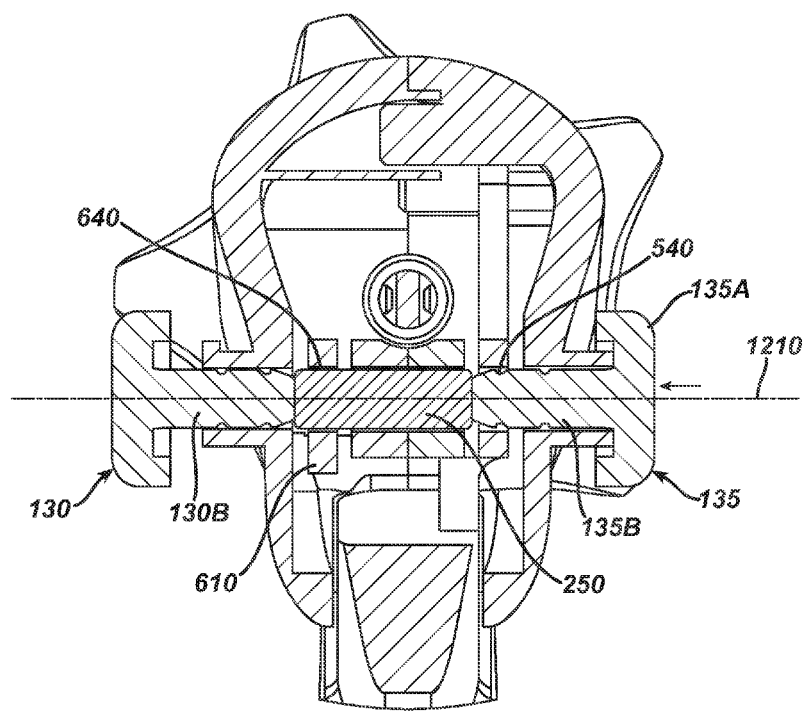
FIG. 12 is a cross sectional view of a toggle-linkage assembly with the finger trigger locked and the thumb trigger in a first position.

To lock finger trigger 120 and utilize thumb trigger 110 to actuate instrument 100, toggle 135 is depressed medially as is shown in FIG. 12. Toggle stud 135B engages pin 250 moving pin 250 medially along axis 1210 resulting in a first position. Medial movement of pin 250 moves toggle 130 laterally disengaging toggle stud 130B from annulus 640. Pin 250 engages annulus 640 permitting thumb trigger 110 to move link 230 via pin 250. When toggle 135 is fully depressed, toggle stud 135B enters annulus 540 of finger trigger linkage 525, locking finger trigger 120 in a fixed position relative to shroud 150B. Thumb trigger 120 can be pivoted about an axis defined by annulus 660 and projection 630 thereby moving link 230 longitudinally translating longitudinal movement to pushrod 210 via ball 240.

Figure 13:
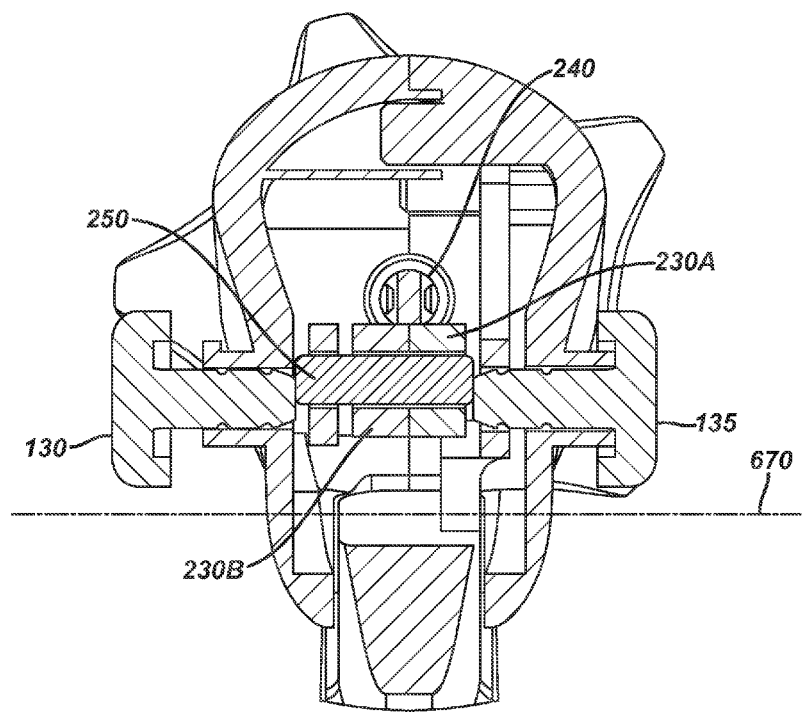
FIG. 13 depicts the FIG. 12 cross sectional view with the thumb trigger moved to a second position.

FIG. 13 depicts pin 250 and link 230 in a second position after movement of thumb trigger 110. When thumb trigger 110 is moved to a second position, annulus 660 and projection 630 rotate about axis 670 and trigger 110 pivots relative to axis 670 generating longitudinal and vertical movement of link 230. Link 230 vertical and longitudinal translation about ball 240 creates a longitudinal force along pushrod 210. In this configuration, longitudinal force is translated along pushrod 210 to end-effector 160.

Figure 14:
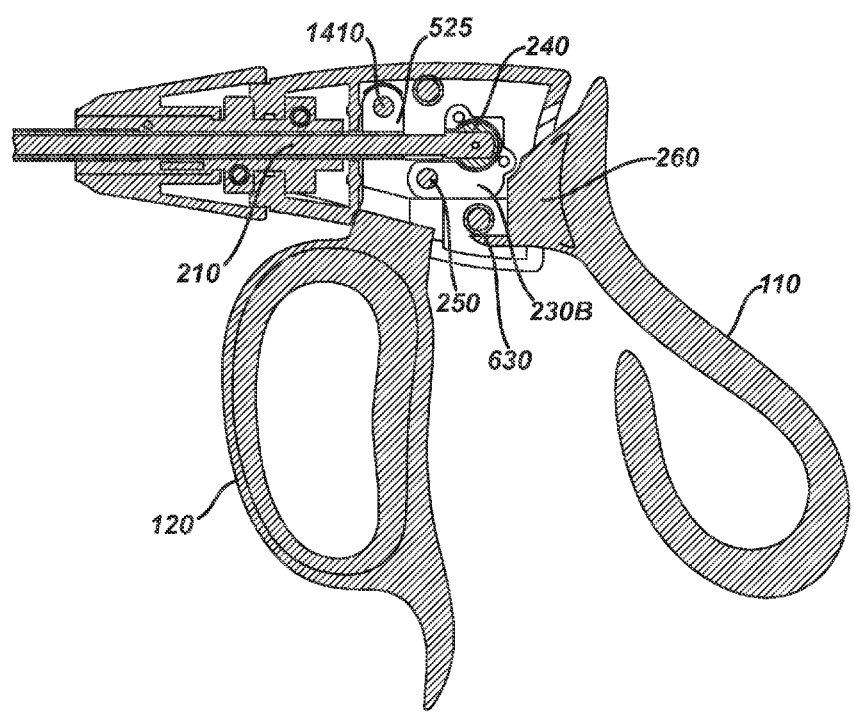
FIG. 14 is a cross sectional view of a surgical instrument having a dual action handle assembly.

FIG. 14 depicts a cross sectional view of a surgical instrument having a dual action handle assembly. In this view, linkage 525 engages boss 1410 on shroud 150B medial surface. Boss 1410 serves as a pivot point for trigger 120 when pin 250 is engaged with annulus 540. Projection 630 engages a depression in shroud 150A (not shown) to permit trigger 110 to pivot when trigger 110 is engaged with link 230 via pin 250. As shown, trigger 110 is in a proximal position and has moved link distally which in turn moves pushrod 210 distally opening end-effector 160. It is contemplated that longitudinal motion along pushrod 210 may either open or close end-effector 160 and is dependent upon end-effector 160 configuration.

When utilizing instrument 100 in surgery, a surgeon obtains instrument 100, and in laparoscopic surgery, introduces shaft 140 into a trocar moving end-effector 160 to an operative site. Depending upon surgeon comfort and instrument 100 orientation, the surgeon may depress toggle 130 to lock thumb trigger 110 in a fixed position relative to shroud 150 which, in turn, permits surgeon to utilize finger trigger 120 to actuate end-effector 160. If the surgeon desires to utilize thumb trigger 110 to actuate end-effector 160, the surgeon depresses toggle 135 which locks finger trigger 120 in a fixed position relative to shroud 150 while simultaneously moving pin 250 in link into engagement with thumb trigger 110, as described above. Surgeon may then move thumb trigger 110 to actuate end-effector 160.

Among other advantages, the toggling mechanism provides an improved ergonomic handle for surgeons. For instance, by actuating the toggle a surgeon can select which trigger will be active or locked based on a surgeon's preference. One surgeon may prefer using the thumb to actuate the end effector, while another surgeon may prefer using fingers. As another example, during a surgical procedure a device may be actuated multiple times potentially resulting in fatigue in the surgeon's hand. By actuating the toggle the surgeon can easily switch the active lever thus providing relief to a fatigued hand.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:
1. An ergonomic surgical instrument comprising:
a shroud have a lateral surface;
a first trigger pivotally connected to the shroud;
a second trigger pivotally connected to the shroud;
a link located within the shroud;
a shaft in communication with the link capable of transferring motion to an end-effector;
an end-effector disposed at a distal end of the shaft wherein movement of the second trigger creates longitudinal force along the shaft moving the end-effector;

a first toggle switch and a second toggle switch disposed substantially opposite each other on the shroud's lateral surface, the first and second toggle switches defining an axis;

a first toggle position wherein the first toggle switch engages the second trigger fixing the second trigger relative to the shroud and moving the in into engagement with the first trigger permitting the first trigger to move the link; and a pin slideably disposed within the link along the axis in mechanical communication with the first and second toggle switches and selectively engageable with the first trigger or the second trigger.

2. The ergonomic surgical instrument of claim 1 further comprising a second toggle position wherein the second toggle switch engages the first trigger fixing the first trigger relative to the shroud and moving the pin into engagement with the second trigger permitting the second trigger to move the link.

3. The ergonomic surgical instrument of claim 1 further comprising an end-effector disposed at the shaft distal end wherein movement of the first trigger creates longitudinal force along the shaft moving the end-effector.

4. The ergonomic surgical instrument of claim 1 wherein the shaft comprises a pushrod.

5. The ergonomic surgical instrument of claim 1 wherein the shaft is adapted for use in endoscopic surgery.

6. The ergonomic surgical instrument of claim 1 wherein the first toggle switch comprises detents to selectively fix the first toggle switch in position relative to the shroud.

7. The ergonomic surgical instrument of claim 1 wherein the end-effector is disposed in a scissor arrangement.

8. The ergonomic surgical instrument of claim 1 wherein the end-effector is comprised of a stationary jaw member and a movable jaw member in mechanical communication with the shaft.

9. A surgical instrument, comprising:
a distal end effector;
a proximal handle comprising a first trigger and a second trigger, each of said triggers being operably connectable to the end effector;
a shroud having a lateral surface;
a link located within the shroud;
a toggle comprising a first toggle switch and a second toggle switch disposed substantially opposite each other on the shroud's lateral surface to define an axis and having a first position and a second position
a pin slidably disposed within the link along the axis in mechanical communication with the first and second toggle switches; wherein
(i) in the first position the first trigger is locked relative the handle and the second trigger is moveable relative the handle to actuate the end effector; and
(ii) in the second position, the first toggle switch engages the second trigger to lock the second trigger relative the handle and moves the pin into engagement with the first trigger to permit the first trigger to move the link and to move relative the handle to actuate the end effector.

10. The surgical instrument of claim 9, further comprising an elongate shaft extending between the end effector and the handle.

11. The surgical instrument of claim 10, wherein the handle and triggers are arranged in a pistol-grip configuration.

12. The surgical instrument of claim 10, wherein the handle and triggers are arranged in a scissors-grip configuration.

* * * * *